United States Patent [19]

Fishman

[11] Patent Number: 5,357,959
[45] Date of Patent: Oct. 25, 1994

[54] ALTERED DIPOLE MOMENT MAGNETIC RESONANCE IMAGING METHOD

[75] Inventor: Royce S. Fishman, Hillsdale, N.J.

[73] Assignee: Praxair Technology, Inc., Danbury, Conn.

[21] Appl. No.: 47,019

[22] Filed: Apr. 16, 1993

[51] Int. Cl.$^5$ .......................................... A61B 5/055
[52] U.S. Cl. .............. 128/653.2; 128/653.4; 424/9
[58] Field of Search .............. 128/653.2, 653.4; 424/9; 436/173

[56] References Cited

U.S. PATENT DOCUMENTS

| 4,586,511 | 5/1986 | Clark, Jr. .............................. 128/653 |
| 4,893,627 | 1/1990 | Kehayias et al. ..................... 128/654 |
| 5,046,498 | 9/1991 | Fishman .......................... 128/653 CA |
| 5,099,834 | 3/1992 | Fishman ............................ 128/203.12 |
| 5,186,924 | 2/1993 | Fishman ................................... 424/9 |

FOREIGN PATENT DOCUMENTS

47692  9/1988  Japan .

OTHER PUBLICATIONS

Rockoff, et al., Evaluation of Xenon as a Roentgenographic Contrast Material, Am. Rev. of Respiratory Disease, vol. 86, pp. 434–438, Jan. 26, 1962.
Hendrick, et al., Introduction To Magnetic Resonance Imaging, Multi-Media Publishing Inc., pp. 7–30 (1984).

*Primary Examiner*—Ruth S. Smith
*Attorney, Agent, or Firm*—Stanley Ktorides

[57] ABSTRACT

A diagnostic medical magnetic resonance imaging and quantitative method for use with human and veterinary subjects in the diagnostic evaluation of normal, altered or diseased status of tissues and fluids containing lipids and or proteins by physically combining stable xenon and/or stable krypton in lipid and lipid containing structures in which they are soluble and physically combining stable xenon and/or stable krypton in protein structures comprised of molecules having nuclei with dipole moments which are altered by their physical incorporation of stable xenon and/or stable krypton in their structures when exposed to a magnetic field thus providing positive contrast enhancement to an image produced by magnetic resonance and the ability to quantify and measure physiology by magnetic resonance.

19 Claims, 2 Drawing Sheets

ALTERED DIPOLE MOMENT MAGNETIC RESONANCE IMAGING METHOD

TECHNICAL FIELD

This invention relates generally to magnetic resonance imaging.

BACKGROUND ART

Recently magnetic resonance imaging (MRI) was commercially introduced to the medical field. MRI is a three dimensional imaging process. MRI is advantageous over other imaging procedures such as two dimensional and three dimensional CT X-ray techniques in that MRI better defines soft tissue structures. It is also advantageous over X-ray techniques, because it does not require the patient being exposed to X-rays.

The likelihood of an accurate diagnosis and assessment of therapeutic impact may be improved in MRI by the use of a contrast enhancement agent. At present, only ionic and nonionic forms of gadolinium based paramagnetic products which must be injected and so are invasive are authorized for use as a contrast enhancement agent with MRI. Such agents are not known to bind or combine with proteins or lipids. Gadolinium is a highly effective relaxation agent on surrounding biological fluids or structures and its use has been authorized to provide contrast enhancement when used with MRI in those intracranial lesions with abnormal vascularity or those thought to cause an abnormality in the blood-brain barrier and to facilitate visualization of intracranial lesions including but not limited to tumors. This contrast enhancer is an intravascular agent and cannot cross the blood-brain barrier unless the blood-brain barrier is damaged. It is also authorized for use in the detection of lesions of the spine. It is therefore limited in application, and provides information that is morphological and anatomical, rather than physiological. Potential side effects and adverse reactions exist.

Recently there has been proposed the use of stable neon as a contrast enhancement agent for MRI. This is discussed in U.S. Pat. No. 5,046,498. While the use of stable neon provides certain advantages for contrast enhancement in carrying out MRI, its use has certain limitations. Because neon is not polarizable its use is limited to establishing reverse contrast. Furthermore, neon is not easily soluble in lipids, thus requiring that high concentrations be used and limiting its usefulness to that of a blood pool flow imaging agent due to the administration times that would be required to achieve adequate saturation of the lipid component of tissues, and again only for reverse contrast enhancement.

Accordingly, it is an object of this invention to provide magnetic resonance imaging with improved positive contrast enhancement and with wider applicability over known procedures.

It is another object of this invention to provide a contrast enhancement agent which will enable improved positive contrast enhancement for magnetic resonance imaging and have wider applicability over known contrast enhancement agents.

It is a further object of this invention to provide magnetic resonance imaging with improved contrast enhancement while also obtaining quantitative evaluation of physiology.

SUMMARY OF THE INVENTION

The above and other objects which will become apparent to one skilled in the art upon a reading of this disclosure are attained by the present invention one aspect of which is:

A method for carrying out magnetic resonance imaging with improved positive image contrast and quantitative evaluation of physiology said method comprising:

(A) providing a living organic subject having molecules comprised of nuclei with dipole moments;

(B) providing stable xenon to said subject and physically combining stable xenon with structures comprised of said molecules and at least one of lipids and proteins;

(C) applying a magnetic field to the subject and altering the dipole moment in at least some nuclei of said molecules by the secondary effect of stable xenon on the resonance of said structures;

(D) providing radio energy for adsorption and reemission by said altered dipole moment nuclei; and (E) gathering data based on the re-emitted radio energy to produce a magnetic resonance image.

Another aspect of the invention is:

A method for carrying out magnetic resonance imaging with improved positive image contrast and quantitative evaluation of physiology said method comprising:

(A) providing a living organic subject having molecules comprised of nuclei with dipole moments;

(B) providing stable krypton to said subject and physically combining stable krypton with structures comprised of said molecules and at least one of lipids and proteins;

(C) applying a magnetic field to the subject and altering the dipole moment in at least some nuclei of said molecules by the secondary effect of stable krypton on the resonance of said structures;

(D) providing radio energy for adsorption and reemission by said altered dipole moment nuclei; and (E) gathering data based on the re-emitted radio energy to produce a magnetic resonance image.

Yet another aspect of the invention is:

A mixture comprising from at least 20 to less than 40 mole percent stable xenon, from 40 to 60 mole percent stable krypton and from 20 to 40 mole percent oxygen.

As used herein, the term "stable xenon" means the naturally occurring non-radioactive forms of xenon having an atomic number of 54 including xenon 131 having an atomic weight of about 131.

As used herein, the term "stable krypton" means the naturally ocurring non-radioactive forms of krypton which have an atomic number of 36.

As used herein, the term "structure" means a compartment of a living organic subject, such as an organ or the arterio-venous system, composed of cells, tissues, and fluids.

As used herein, the term "secondary effect" means the resonance of a structure itself due to its being combined with xenon or krypton. This differs from the primary effect which refers to the resonance of a contrast agent which may be in the vicinity of a structure.

As used herein, the term "blood-brain barrier" refers to the fact that the cells of brain capillaries are different from other capillaries, because they form a continuous wall that prevents many substances from entering the brain. The blood-brain barrier is that continuous wall which exists without interruption except in case of disease. Essential nutrients and gases can still cross the normal blood-brain barrier. Molecules that are lipid soluble are easily transported across the blood-brain barrier. Certain gases can diffuse across the blood-brain barrier.

As used herein, "lipoprotein" means the class of conjugated proteins composed of a complex of protein and lipid and separable on the basis of solubility and mobility properties.

As used herein, "phospholipid" means any of numerous lipids in which phosiric acid and as well as a fatty acid is esterified to glycerol and which are found in all living cells and in the bilayer of plasma membranes.

As used herein, "plasma membrane" means a semipermeable limiting layer of cell protoplasm consisting of 3 molecular layers of which the inner and outer are composed of protein, while the middle layer is composed of a double layer of fat (lipid) molecules.

As used herein, "saturation" when it is applied to the presence in cells and tissues of a substance such as an MRI contrast agent, means that the maximum amount of the MRI contrast agent that can be present in a specific type of cellular and/or tissue structure based on the dosage administered has been achieved. This may occur for example due to the solubility of the MRI contrast agent in lipid containing cells and tissues. Each type of normal or abnormal cell or tissue based on its lipid content may require different lengths of time to achieve saturation.

As used herein, the term "in-vivo" refers to being inside the body.

As used herein, the term "nucleus" (plural nuclei) means the positively charged central portion of an atom that comprises nearly all of the atomic mass and that consists of protons and neutrons, except in hydrogen, whose nucleus consists of only one proton. The properties of nuclei that are relevant to MRI include their magnetic dipole moments and presence in living tissue. Nuclei possess magnetic dipole moments, meaning they produce a magnetic field themselves and can be affected by an externally imposed magnetic field. The magnetic dipole moments of protons and neutrons pair up and cancel each other out. If a nucleus has an equal number of protons and neutrons, then there is no magnetic dipole moment. If a nucleus has an odd number of protons or neutrons, then a net magnetic dipole moment exists that can be effected by an external magnetic field such as that imposed by MRI. Hydrogen, Carbon 13, Sodium 23 and Phosphorous 31 are examples of nuclei that are both present in living tissue and may be utilized for MRI procedures.

As used herein, "$T_1$ relaxation" (spin-lattice) means the rate of recovery of the longitudinal magnetization described by the longitudinal relaxation time. It is the time required for about 63% of the longitudinal magnetization to recover along the direction of the static magnetic field after a 90° pulse. Different $T_1$ recovery rates exist because different tissues have different concentrations and sizes of macromolecules. $T_1$ weighted images are best for obtaining high resolution anatomy.

As used herein, "$T_2$ relaxation" (spin-spin) means the loss of signal due to inherent tissue effects. It is the time required for the transverse magnetization to decrease to 37% of its original value which it possessed immediately following the 90° pulse. Tissues have different $T_2$ values, mostly due to their differing macromolecular environments. $T_2$ is better than $T_1$ for differentiating tissue and so is effective in detecting disease.

As used herein, "pulse sequence" refers to how radiofrequency pulses are sent into a patient, how the signals are re-emitted from the patient and how much time exists between the sending and receiving of the pulses. There are many factors that are manipulated by the clinician using the MRI device itself, which allow the pulse sequence to be varied.

As used herein, the term "injection" means the act of forcing a fluid or solution into an artery, vein, cavity or tissue to introduce a gas or solution. Injections are done rapidly over a period of time ranging from seconds to generally less than one minute.

As used herein, the term "infusion" means the introducing of a gas or gas in solution into an artery, vein, cavity or tissue over a long period of time generally measured in minutes.

As used herein, the term "non-invasive" means not requiring breaking the integrity of the body surface such as is required with an injection, to administer a substance. Inhalation of a gas is a non-invasive procedure, because the gas is inhaled during the normal act of breathing. Procedures that are invasive carry with them added risk of problems at the injection site and the breaking of the sterility of the arterio-venous system.

As used herein, the term "physically combining" means the physical occupation by stable xenon and/or stable krypton of cavities in proteins, the temporary binding of xenon and/or krypton with proteins by weak van der Walls and other coulombic forces, and the solubility of stable xenon and/or stable krypton in lipids.

As used herein, the term "solubility" of a gas means the ability of a substance such as a specific volume of gas to be dissolved in a specific volume of liquid, thereby forming a solution which is a mixture of the two substances.

As used herein, the term "equilibrated solution" means a solution in which the ratio of concentration of gas in a solution equals that of the gas above the solution.

As used herein, the term "saturated solution" means a solution that contains as much of the gas as it can in the presence of an excess of the gas. The saturated solution is then kept in a gas tight sealed container with no gas space and is injected or infused directly into the patient.

As used herein, the term "supersaturated solution" means a solution that goes beyond saturation, because, for example, the pressure and/or temperature is increased so that the amount of gas present in the solution is above that which it would be at standard temperature and pressure. The supersaturated solution is then kept in a gas tight sealed container with no gas space under increased pressure and/or temperature and is injected or infused directly into the patient.

As used herein, a "sealed cartridge" as a form of product packaging means a container impermeable to gas that may be filled with stable xenon or krypton gas or gas mixture in an equilibrated, saturated or supersaturated liquid solution and then sealed during the production process. The cartridge is used with a device that breaks the seal of the cartridge and allows the injection or infusion of its contents directly into a patient.

As used herein, a "pre-filled syringe" means a form of product packaging where the syringe is made of a material that is impermeable to gas. It may be filled for example with stable xenon gas or gas mixture or stable xenon gas or gas mixture in an equilibrated, saturated or supersaturated liquid solution and then sealed during the production process. The syringe contains two septa, one in the rear and one in the front, that act after production filling of the syringe as seals to prevent the escape of gas from the inside of the syringe, or the escape of gas from solution by eliminating any space around the liquid. At the time of injection, the front septa is penetrated by an internal extension of the external needle. The pressure from the rear septa moving forward drives the gas or solution out the front needle directly into a patient.

DETAILED DESCRIPTION

Magnetic resonance imaging or MRI takes advantage of the fact that diseased tissue and different types of healthy tissue have a differing molecular arrangement and thus produce a differing image when re-emitting radio wave energy.

Certain types of nuclei, including but not limited to hydrogen nuclei, when placed in a uniform magnetic field, emit a pulse of radiofrequency after they are exposed to a pulse of radiofrequency. This is referred to as "resonance", can be measured and can provide information about the nuclei that emitted them.

Figure 1:
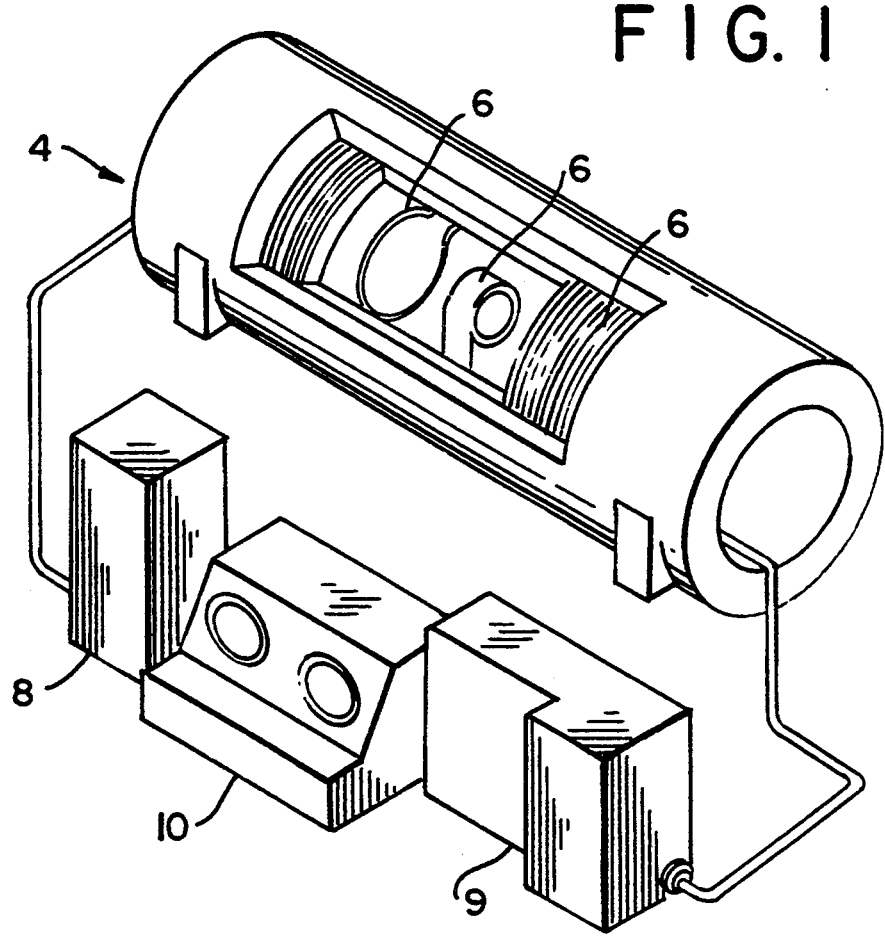
FIG. 1 is a simplified and generic schematic diagram of a superconductive MRI apparatus which may be employed in the practice of this invention. Specific MRI designs vary between manufacturers, from model to model from a single manufacturer, and may use superconductive, permanent or resistive types of magnets.
Figure 2:
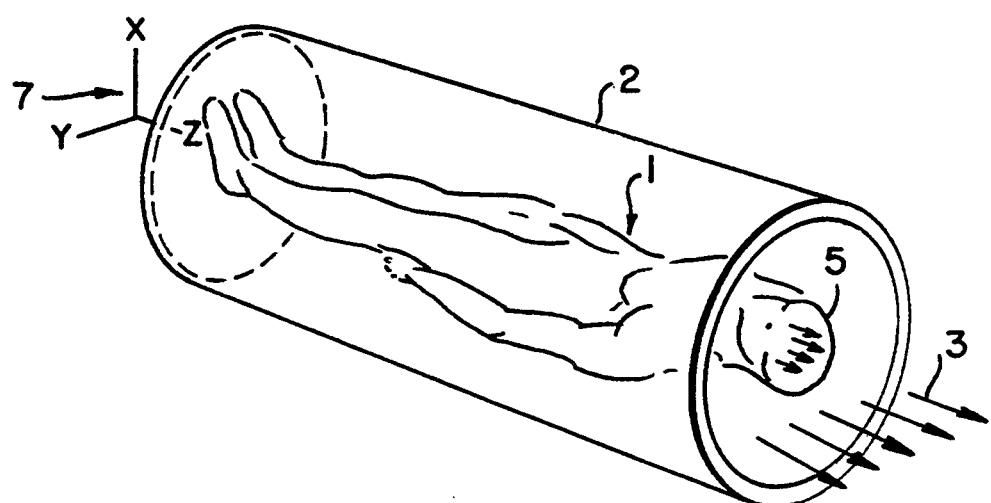
FIG. 2 is a simplified representation of a human subject undergoing a step in MRI imaging with alignment of nuclei.

Referring now to FIGS. 1 and 2, in the practice of MRI, a human or veterinary patient 1 is placed in the center or bore 2 of a magnetic field 3 generated by an MRI system 4. The nuclei in the patient, which are normally randomly arranged, are subjected to a strong magnetic field, which causes some of them to align 5 their spin axes along the magnetic field. Radiofrequency is emitted by coils 6 that are either inside the MRI system near but not on the patient, or that are actually placed on the patient for imaging smaller more focused areas. The same or additional coils may be used to receive the resonating signal that is emitted by the nuclei. A series of radiofrequency pulses are then emitted by the power supply 8 of the MRI system via these coils. The nuclei in the body absorb this energy and the vector of their magnetization is briefly rotated. When the radiofrequency pulse is turned off, the nuclei return to their previous condition (equilibrium) and in the process of doing so reemit the energy, producing a radio frequency pulse (resonance) which is collected as data and converted by MRI computer software to useful information having medical value in patient management.

The specific characteristics of the radiofrequency emitted indicate the quantity and nature or state of the atoms in the specific areas of tissue being examined. The source of a specific resonating signal is established as to its location in three dimensions. Additional magnet coils are used to make the field generated by the main magnet vary in small increments along three coordinates 7, which are called gradients. The frequency of the radiofrequency pulse is linked to these magnetic gradients. They allow image reconstruction by the MRI computer software. The information produced is processed by a computer 9 and special software programs to produce, on display 10, images of tissues in the body and other information and may be used to derive quantitative information of a physiological nature.

MRI imaging is based on four important parameters. These are proton density, $T_1$, $T_2$ and flow parameters. Pulse sequences made up of radiofrequency pulses can vary in number, the time it takes for the resonance signal to be emitted and the time interval between pulses. The most common pulse sequences are commonly called spin echo, saturation recovery and inversion recovery. Preferably, hydrogen nuclei are imaged because they produce the most powerful response signal and exist in all body tissues, primarily as part of the water molecule.

In the practice of this invention, initial baseline MRI images of the patient may optionally be taken without stable xenon and/or stable krypton being provided to the patient, followed by stable xenon and/or stable krypton being provided to the patient so that it is present in-vivo during that part of the MRI procedure whose purpose it is to generate images and quantitative information based on the in-vivo presence and distribution of stable xenon and/or stable krypton and the effect of stable xenon and/or stable krypton on the dipole moment of nuclei of the structure it is physically combined with. The stable xenon and/or stable krypton is provided in an amount sufficient to effectively achieve enhanced contrast results. However, stable krypton at the same concentration and pressure in blood provides about one half the positive contrast as an equal concentration of stable xenon at a comparable pressure. It has been found that the use of stable xenon and/or stable krypton using, for example, but not necessarily limited to, $T_2$ weighted images, produces positive contrast. The positive contrast produced where stable xenon and/or stable krypton is present is in a high enough ratio to the normal image produced where stable xenon and/or stable krypton is not present, to allow after the data is processed a clear visualization of where it is present and not present based on the secondary effect of the stable xenon and/or stable krypton and not on the primary resonance of the gas. This contrast may be used to better distinguish different normal tissues and compartments from each other, as well as normal from abnormal tissues, compartments and physiology. MRI procedures may be performed during but not limited to the wash-in, equilibrium and/or washout phases of xenon and/or krypton being present in-vivo. Manipulation of the data produced by an MRI computer and software can include but is not limited to the subtraction of baseline MRI images taken without stable xenon and/or stable krypton in-vivo in the patient from those taken with stable xenon and/or stable krypton present in-vivo in the patient, and/or the use of regions of interest to analyze specific areas of any and all images either separately and combined through the use of the MRI computer and software to generate images and/or quantitative data that is of diagnostic and physiological value.

The application of the contrast enhancement agent or agents when used with an MRI system, suitable methodologies and software may include but is not limited to qualitative and quantitative determinations of one or more of gray and white matter brain function, local, regional and global cerebral blood flow rate and cerebral blood flow, MR angiographic time of flight related studies, steady state cerebrovascular measurements of neurobehavorial stimulation, evaluation of the microvasculature of the brain for changes including but not limited to cerebral blood volume and cerebral blood flow transit times, brain tissue perfusion, blood pool status in other areas of the body, blood flow transit times in other areas of the body, a preferential biologic distribution pattern in other areas of the body, tissue blood volume in other areas of the body, tissue perfusion and function in other areas of the body, in the diagnostic evaluation of a patient upon presentation to detect abnormalities, determine disease states, and their status for use in therapeutic decision making for a patient including but not limited to physiological challenges and the evaluation of the effectiveness of the therapy(ies) implemented. In addition to brain and cerebrovascular related applications, other applications of the invention include but are not limited to evaluations of the heart, liver and kidneys.

While not wishing to be held to any theory, it is postulated that stable xenon and in particular xenon 131 which has a sizeable quadropole moment and highly polarizable nucleus, and to a lesser degree stable krypton, alters the response of red blood cells containing globin protein and plasma lipids in the blood, lipoproteins, cells containing lipids and/or phospholipids, and tissues containing cells with lipids and/or phospholipids, to magnetic fields and one or more MRI imaging modalities, by changing their dipole moment thereby interfering with and lengthening their relaxation time. Thus, it is the secondary effect of stable xenon and/or stable krypton on tissues and fluid components it is physically combined with rather than the primary resonance of the gas that is being imaged. Stable xenon, uniquely among the rare gases such as neon and krypton, is a mild to potent anesthetic at moderately high to high concentrations. Some of the properties that make stable xenon an anesthetic agent, may also result in it providing greater contrast than stable krypton at the same concentration but both are still effective MRI contrast agents that uniquely reflect both physiology and morphology. Anesthetics interact with hemoglobin, and by inference are capable of interacting with other proteins. While being administered to a patient, stable xenon is able to transiently enter and occupy certain existing cavities in the globin protein structure of red blood cells such as hemaglobin and myoglobin, with the major component of bonding energy being the London type of van der Waal's interactions, which are weak electric forces. Stable xenon is soluble in lipids. Lipids are present in the plasma of blood. Therefore, an alteration in dipole moment of nuclei of molecules in blood exposed to a magnetic field and specific pulse sequence occurs when the red blood cells and plasma lipids within the blood contain stable xenon. Lipids are also present in cells and the tissues they comprise in differing percentages and forms. Stable xenon during administration to the patient, by physically combining, transiently becomes physically part of the lipid and/or phospholipid components of cells, and/or a tissue structure that contains both protein and lipid such as a lipoprotein and/or plasma membrane, and alters the response of that cell or tissue to a magnetic field and a specific pulse sequence. In addition, stable xenon may undergo active transport into intracellular water and be reflective of the energetic metabolism of the cell. By varying the concentration of stable xenon administered which effects the amount of stable xenon potentially present in a specific type of cell at equilibrium, and the administration time of stable xenon which is required to achieve saturation of a particular type of cell, certain tissues containing those cells in which stable xenon is physically present can be contrasted with other tissue where it is not, or, which due to the unique nature of that normal or abnormal tissue will contain more or less stable xenon than another type of tissue.

The same postulation as described above for stable xenon, applies to stable krypton with the following considerations. Stable krypton is less soluble in lipids than stable xenon, and therefore has less of an effect on the dipole moment of lipids. This may be compensated for by increasing the concentration of stable krypton used up to 80 percent without concern for patient safety, since unlike stable xenon, stable krypton is not anesthetic at high concentrations. Stable krypton also has less of an effect on the dipole moment of a protein such as the globin portion of hemaglobin. Stable krypton has a different atomic weight, atomic mass, relative sensitivities to constant fields and frequencies, and other properties, then stable xenon. The properties unique to stable krypton, combined with their being a fixed number of cavities in a protein structure which stable krypton can temporarily occupy and be physically bound in, may contribute to stable krypton having less of an impact on the dipole moment of a protein structure regardless of the concentration used. It is postulated that the above may be the cause of stable krypton generating less positive contrast than stable xenon in a blood sample.

The stable xenon and/or stable krypton may be provided to the living organic subject as pure stable xenon and/or stable krypton or as a mixture with one or more other gases such as oxygen, helium, nitrogen or carbon dioxide which are medically pure, commonly referred to as USP or NF. For example, the stable xenon and/or stable krypton may be provided to the patient by inhalation of one hundred percent concentration of pure stable xenon and/or stable krypton gas alternated with a one hundred percent concentration of pure (medical) oxygen gas, or by inhalation of a mixture of stable xenon and/or stable krypton gas and another gas or gases.

The stable xenon and/or stable krypton may be provided to the living organic subject as a gas mixture which may be premixed in a container such as a gas cylinder or may be made up at the use site from containers of the individual gases. If provided as a gas mixture, the mixture, comprises from 10 to 80.5 percent, preferably from 33 to 80.5 mole percent xenon and/or stable krypton, and from 19.5 to 90 mole percent oxygen (medical or USP grade), preferably from 19.5 to 67 mole percent oxygen. The mixture may also contain helium which, if present, can be at a concentration of up to 70.5 mole percent, preferably at a concentration within the range of from 1 to 42 percent.

A particularly preferred mixture comprises both stable xenon and stable krypton along with oxygen. A sufficient concentration of stable xenon is provided to provide good contrast enhancement without causing an excessive anesthetic effect on the patient. Stable krypton, which is not anesthetic, improves the contrast enhancement effect and oxygen provides life support to enable a prolonged procedure. This mixture comprises from at least 20 to less than 40, preferably from 25 to 33 mole percent stable xenon, from 40 to 60, preferably 47 to 55 mole percent stable krypton, and from 20 to 40, preferably about 20 mole percent oxygen.

Xenon is a relatively heavy gas. This may make it difficult to breathe for some patients for extended periods of time at high concentrations. It also causes xenon to sink due to gravity to the lowest part of the lungs, whether the patient is lying on their back, stomach, or, is sitting up. In such cases, adding helium to the mixture of stable xenon and/or stable krypton with or without oxygen may be useful in reducing the density of the gas mixture, facilitating the ability of the patient to breathe, and improving the distribution of stable xenon over a greater percentage of the alveolar-capillary membrane in the lung across which xenon may be exchanged. The mixture containing stable xenon and/or stable krypton with or without oxygen may also contain carbon dioxide which, if present, can be at a concentration of up to 7 mole percent, preferably at a concentration within the range of from 0.2 to 5 mole percent. The carbon dioxide may be useful to induce breathing in a patient and thus facilitate the passage of the xenon into the patient or as part of a carbon dioxide responsiveness test. The stable xenon and/or stable krypton mixture may also contain nitrogen, such as when the mixture is made up using air. If present, the nitrogen can be at a concentration of up to 70.5 percent and preferably at a concentration within the range of from 1 to 40 percent. If air is used to make up the xenon mixture, the mixture may have present other species in small amounts which may be found in air.

Figure 3A:
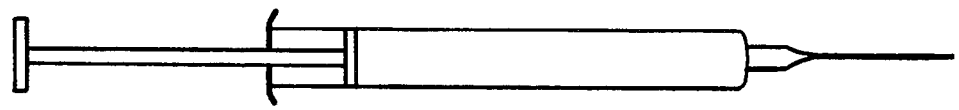
FIG. 3A is a simplified and generic schematic diagram of a medical syringe with needle which may be used for bolus injections or infusion for use in the practice of the invention.
Figure 3B:
FIG. 3B is a simplified representation of a syringe into which stable xenon and/or stable krypton is provided from a sealed vial or cartridge.

The stable xenon and/or stable krypton may be provided to the subject in any effective manner. For example, the stable xenon and/or stable krypton may be provided to the patient by sterile injection of a bolus or infusion using a syringe or other suitable method, wherein the stable xenon and/or stable krypton is injected or infused using sterile technique as a gas or in an equilibrated, saturated or supersaturated solution of sterile water, sterile saline, whole blood or biologic components of blood by syringe, as illustrated in FIG. 3A, or other means of intravenous and/or intraarterial injection or infusion. The stable xenon and/or stable krypton may be provided to the syringe from a sealed vial or other container as illustrated in FIG. 3B. The stable xenon and/or stable krypton gas and/or gas in solution may be provided to the organic subject in ready to use pre-packaged form in a sterile syringe or cartridge for use with an injection device if the product form allows pre-packaging, provides extended shelf life and can be easily shipped with adequate controls. The syringe or other suitable method of injection or infusion may also be prepared from stable xenon and/or stable krypton gas contained in a sterile vial, disposable or returnable compressed gas cylinder, or stable xenon gas from one of those sources or one or more components including but not limited to sterile water, sterile saline, whole blood or biologic components of blood, so long as the final product injected is sterile and aseptic technique is used.

One advantage of the invention is that the contrast enhancement agent need not be administered invasively by intravenous injection or infusion, does not require the withdrawal of human blood and in vitro preparation of the patient's red blood cells with a metallic ion or other element or compound, and does not involve the use of externally sourced biologics as, for example from a vial, such as albumin which can introduce an element of risk into the procedure.

Figure 4:
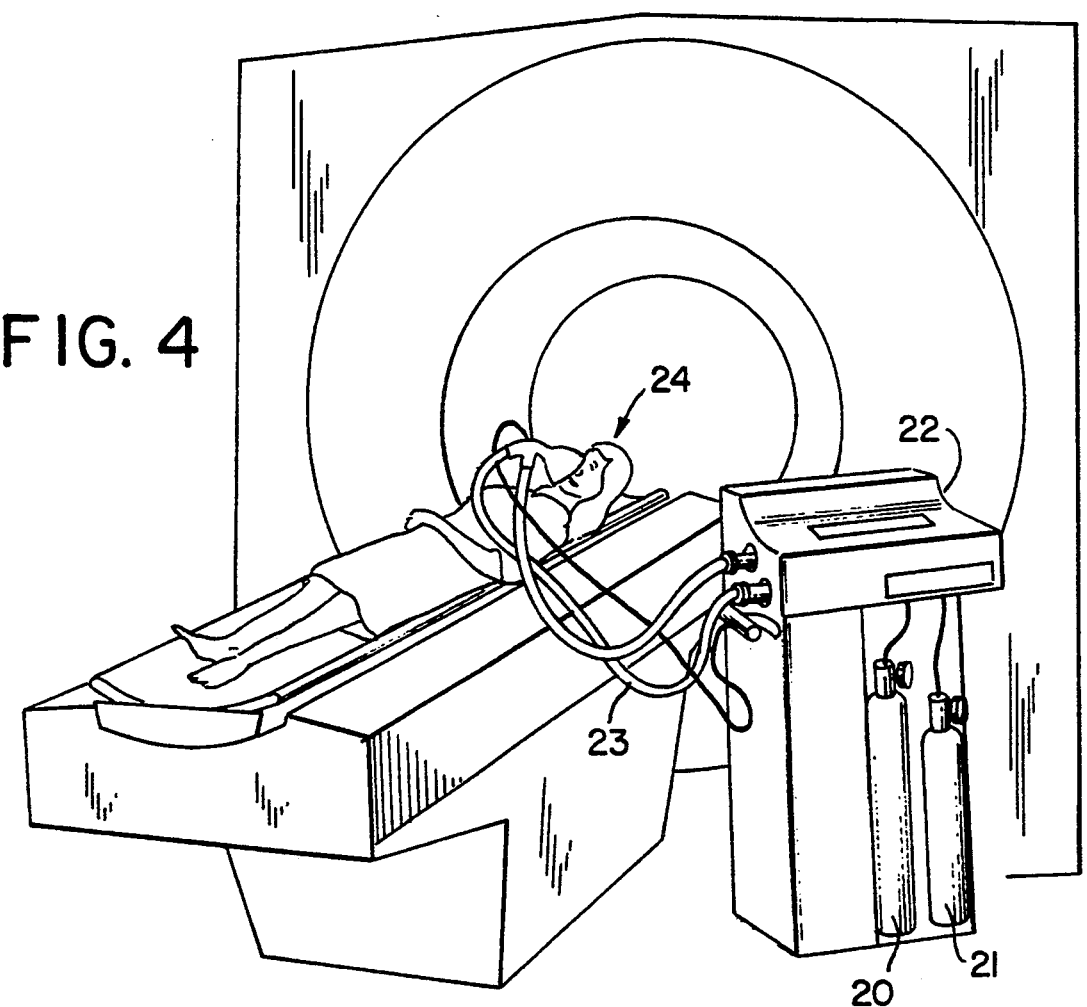
FIG. 4 is a representation of a human subject being given a gas mixture in the practice of the invention.

The stable xenon and/or stable krypton may be delivered to the person or animal non-invasively by alternating inhalation of one hundred percent concentration of stable xenon or stable krypton or a mixture comprising or consisting essentially of stable xenon and stable krypton with inhalation of one hundred percent concentration of oxygen during the respiratory cycle, or as part of a gas mixture directly from a cylinder that is pre-mixed with a specific gas mixture containing fixed concentration of each component or, from a large gas tight plastic bag that is filled by the manufacturer or the user from a cylinder that is pre-mixed with a specific gas mixture containing a fixed concentration of each component, or from several cylinders containing one or more of the gas components, or, as illustrated in FIG. 4, from several compressed gas cylinders 20, 21 containing one or more of the gas components which are mixed by a mechanical device 22 and then administered 23 to the patient 24.

The use of helium, if included in the gas mixture, serves to reduce the density of the gas mixture, facilitating the ability of the patient to breathe and improving the distribution of stable xenon and/or stable krypton over a greater percentage of the alveolar-capillary membrane in the lung across which gas may be exchanged.

The use of carbon dioxide, if included in the gas mixture, serves to alter respiration and/or cerebral physiology at the discretion of the clinician.

An advantage of the practice of this invention is that it enables an MRI system to generate physiological information in addition to anatomical information, thereby allowing a more accurate evaluation of the relative functioning of cells, tissues, organs, organ systems and other body compartments.

Another advantage of the practice of this invention is that it is useful for a wide range of applications, including but not limited to evaluation of: cerebral blood flow and brain tissue function in stroke, head trauma, Alzheimers disease, Parkinson's disease, migraine and seizures; MR angiographic time of flight related studies; myocardial blood flow and myocardial infarction; identification of fat in heart muscle; liver blood flow, liver function and fatty infiltration of liver; renal blood flow, especially in transplants, since stable xenon and/or stable krypton being inert and therefore non-toxic after multiple doses, can be used repeatedly without concern for its effect, or of x-ray radiation dose. The large number of uses would reduce the number of different types of MRI contrast agents that need to be purchased and inventoried, thereby helping to reduce the cost of health care.

Stable xenon and stable krypton are useful in the practice of this invention because they are inert, monatomic, lipid soluble and readily diffusible tracers, which associate preferentially with the globin protein portion of red blood cells and are soluble in lipid components of plasma, and therefore are carried by the blood throughout the body. They rapidly cross the blood-brain barrier and are preferentially distributed within the highly lipid cells of the brain. They are also distributed within the other cells, tissues, organs, organ systems and compartments of the body depending on the patency of the blood flow and their lipid content. The lipid content of each type of cell and abnormal cell comprising tissues, organs and organ systems is unique.

Despite their lack of chemical reactivity, stable xenon and stable krypton associate preferentially and transiently by physically combining with the globin portion of red blood cells. The mechanism of association involves a rapidly reversible combination of weak electric van der Waals and other coulombic forces. Stable xenon and/or stable krypton ligands transiently occupy appropriately sized voids in the globin protein structure while it is being administered. Stable xenon and/or stable krypton are also soluble in the lipid components of blood plasma. These factors make stable xenon and/or stable krypton uniquely suitable for evaluating blood flow to, in and from organs systems and compartments such as the brain, liver, myocardium of the heart and kidneys.

An additional advantage of the invention, is that stable xenon and stable krypton can cross the blood barrier and are soluble in brain tissue based on its lipid content, making them suitable for evaluation of brain tissue function by measurement of brain tissue lambda, also known as brain tissue-blood partition coefficient. Because normal gray and white brain matter contains differing concentrations of lipids, and normal and abnormal brain tissue contains differing concentrations of lipids, they can be distinguished from each other.

Stable xenon specifically is also useful in imaging blood vessels by altering the dipole moment of molecules and therefore the contrast of blood vessel walls which are composed of cellular structures contain proteins and lipids with which the stable xenon is physically bound.

Stable xenon is also specifically useful in imaging cerebral blood vessels by increasing the contrast of the blood in the vessels. With an adequate concentration and administration time, stable xenon can increase the rate of cerebral blood flow thereby facilitating time of flight based studies. To this increase in contrast is added the contrast produced by the high concentration of stable xenon in plasma lipids and globin proteins in the blood.

A further advantage of the invention, is that because of its rapid elimination from the body after administration, with for example 95% of stable xenon or stable krypton being excreted on the first pass of blood through the lungs, studies can be rapidly repeated with no risk to the patient. This provides the diagnostic advantage of repeat studies being performed at short intervals to monitor and evaluate rapidly evolving patient conditions, to challenge physiology by altering it by for example manipulating blood pressure or using drugs, and to evaluate the impact of therapy. This is not possible with gadolinium based paramagnetic contrast agents because of their long clearance times from the body.

Another advantage of the invention, is that it allows the physician to directly compare and correlate high resolution anatomical structure imaged by MRI, with physiological information produced by the same MRI, when used with patients to which the invention has been administered. This is an advantage compared to the use of an MRI procedure producing only anatomical information such as is the case with conventional MRI procedures.

The following examples are presented for illustrative purposes and are not intended to be limiting.

EXAMPLE 1

Two whole blood samples were taken from the same human patient and were placed in sealed test tubes. Stable xenon was provided to one sample under pressure and became physically combined with the hemoglobin and plasma lipids components of the blood. This created one sample with blood and xenon and one other with blood and air. After a period of time, both samples underwent MRI imaging using an apparatus similar to that illustrated in FIG. 1 using a specific $T_2$ methodology. The resulting MRI image showed a 17.5% difference in relaxation time between the blood sample containing stable xenon and that containing air.

EXAMPLE 2

A procedure similar to that of Example 1 was carried out except that stable krypton was used in place of stable xenon. The resulting MRI image showed a 9.6% difference in relaxation time between the blood sample containing stable krypton and that containing air.

EXAMPLE 3

A human subject suspected of having suffered a stroke is administered a gas mixture comprising 33 mole percent stable xenon, 25 mole percent oxygen and 42 mole percent nitrogen for a period of 20 minutes, which is sufficient to saturate the hemoglobin and plasma lipid components of blood and subsequently the lipid content of both gray and white brain matter with stable xenon. While the gas mixture administration is continued, and upon the application of a magnetic field and specific $T_2$ pulse sequence, and due to the very high resolution, depth sensitivity and anatomic correlation provided by MRI, the microvascular blood flow in the brain which reflects brain metabolism and the blood:brain partition coefficient (lambda) of the brain cells which reflects brain tissue function is studied to detect the existence of small areas of dead brain tissue known as infarcts prior to the time they would have been detectable without the practice of the invention.

EXAMPLE 4

The procedure described in Example 3 is repeated, except the gas mixture administered to the patient comprises 40 mole percent stable xenon, 25 mole percent oxygen and 35 mole percent helium, with comparable results.

EXAMPLE 5

The procedure described in Example 3 is repeated, except that the gas mixture administered to the patient comprises 80 mole percent stable krypton and 20 mole percent oxygen with comparable results.

EXAMPLE 6

The procedure described in Example 3 is repeated, except that the gas mixture administered to the patient comprises 28 mole percent stable xenon, 52 mole percent stable krypton and 20 mole percent oxygen, thereby maximizing alterations of the dipole moment of lipids and proteins in the blood and lipids in brain tissue while using a concentration of stable xenon that will not result in analgesia or anesthesia during extended periods of administration. MRI images with excellent contrast enhancement are obtained.

Although the invention has been described in detail with reference to certain embodiments, those skilled in the art will recognize that there are other embodiments within the spirit and scope of the claims.

I claim:

1. A method for carrying out magnetic resonance imaging with improved positive image contrast and quantitative evaluation of physiology said method comprising:
   (A) providing a living organic subject having molecules comprised of nuclei with dipole moments;
   (B) providing stable xenon to said subject and physically combining stable xenon with structures comprised of said molecules and at least one of lipids and proteins;
   (C) applying a magnetic field to the subject and altering the dipole moment in at least some nuclei of said molecules by the secondary effect of stable xenon on the resonance of said structures;
   (D) providing radio energy for absorption and reemission by said altered dipole moment nuclei; and
   (E) gathering data based on the reemitted radio energy to produce a magnetic resonance image.

2. The method of claim 1 wherein the stable xenon is provided to the subject invasively by injection or infusion.

3. The method of claim 2 wherein the xenon is provided in gaseous form.

4. The method of claim 2 wherein the xenon is provided as part of an equilibrated, saturated or supersaturated solution.

5. The method of claim 1 wherein the subject is a person or animal and the stable xenon is provided to the subject non-invasively by the breathing in of pure stable xenon alternated with the breathing in of pure oxygen.

6. The method of claim 1 wherein the subject is a person or animal and the stable xenon is provided non-invasively to the subject by the breathing in of a mixture comprising from 10 to 80.5 mole percent stable xenon and from 19.5 to 90 mole percent oxygen.

7. The method of claim 6 wherein the mixture additionally comprises helium in a concentration of up to 70.5 mole percent.

8. The method of claim 6 wherein the mixture additionally comprises carbon dioxide in a concentration of up to 7 mole percent.

9. The method of claim 6 wherein the mixture additionally comprises nitrogen in a concentration of up to 70.5 mole percent.

10. The method of claim 1 wherein the data gathering of step (E) comprises establishing qualitative and quantitative physiological information and an image.

11. The method of claim 1 further comprising providing stable krypton to said subject.

12. The method of claim 11 wherein a mixture comprising from at least 20 to less than 40 mole percent stable xenon, from 40 to 60 mole percent stable krypton and from 20 to 40 mole percent oxygen is provided to the subject.

13. A method for carrying out magnetic resonance imaging with improved positive image contrast and quantitative evaluation of physiology said method comprising:
   (A) providing a living organic subject having molecules comprised nuclei with dipole moments;
   (B) providing stable krypton to said subject and physically combining stable krypton with structures comprised of said molecules and at least one of lipids and proteins;
   (C) applying a magnetic field to the subject and altering the dipole moment in at least some nuclei of said molecules by the secondary effect of stable krypton on the resonance of said structures;
   (D) providing radio energy for adsorption and reemission by said altered dipole moment nuclei; and
   (E) gathering data based on the re-emitted radio energy to produce a magnetic resonance image.

14. The method of claim 13 wherein the subject is a person or animal and the stable krypton is provided to the subject non-invasively by the breathing in of pure stable krypton alternated with the breathing in of pure oxygen.

15. The method of claim 13 wherein the subject is a person or animal and the stable krypton is provided non-invasively to the subject by the breathing in of a mixture comprising from 10 to 80.5 mole percent stable krypton and from 19.5 to 90 mole percent oxygen.

16. The method of claim 15 wherein the mixture additionally comprises helium in a concentration of up to 70.5 mole percent.

17. The method of claim 15 wherein the mixture additionally comprises carbon dioxide in a concentration of up to 7 mole percent.

18. The method of claim 15 wherein the mixture additionally comprises nitrogen in a concentration of up to 70.5 mole percent.

19. The method of claim 13 wherein the data gathering of step (E) comprises establishing qualitative and quantitative physiological information and an image.

* * * * *